United States Patent [19]

Ong

[11] Patent Number: 4,812,309
[45] Date of Patent: Mar. 14, 1989

[54] GEL INSECTICIDAL COMPOSITIONS

[75] Inventor: Chungjian J. Ong, Somerville, N.J.

[73] Assignee: American Cyanamid Company, Stamford, Conn.

[21] Appl. No.: 878,911

[22] Filed: Jun. 26, 1986

Related U.S. Application Data

[63] Continuation-in-part of Ser. No. 764,363, Aug. 12, 1985, abandoned.

[51] Int. Cl.$^4$ .............................................. A01N 25/00
[52] U.S. Cl. ...................................... 424/84; 514/275; 514/944
[58] Field of Search ................... 424/84; 514/944, 975

[56] References Cited

U.S. PATENT DOCUMENTS

| | | | |
|---|---|---|---|
| 4,163,102 | 7/1979 | Lovell | 544/330 |
| 4,213,988 | 7/1980 | Lovell | 514/275 |
| 4,320,130 | 3/1982 | Baisley et al. | 424/84 |
| 4,332,792 | 6/1982 | Kohn et al. | 424/84 |
| 4,495,168 | 1/1985 | Schmolka | 424/45 |
| 4,545,992 | 10/1985 | Kamishita | 514/944 |

FOREIGN PATENT DOCUMENTS

| | | | |
|---|---|---|---|
| 0114504 | 7/1982 | Japan | 424/84 |
| 0061518 | 4/1985 | Japan | 514/944 |

*Primary Examiner*—Leonard Schenkman
*Attorney, Agent, or Firm*—Alice C. Brennan

[57] ABSTRACT

An insecticidal gel composition comprising on a weight basis 14% to 22% of the gellant α-hydro-Ω-hydroxypoly(oxyethylene)poly(oxypropylene(poly(oxyethylene) block copolymer having an average molecular weight 12,500, mp 56° C., Brookfield viscosity of 3100 at 77° C., and surface tension of a 0.1% aqueous solution: 40.6 dynes/cm: 0% to 0.5% propyl p-hydroxybenzoate; 0% to 30% propylene glycol; 0.5% to 6% of a $C_{17}$-$C_{19}$ unsaturated fatty acid; a $C_7$-$C_{17}$ saturated fatty acid or a mixture of the fatty acids; 1% to 5% of formula (I) insecticide:

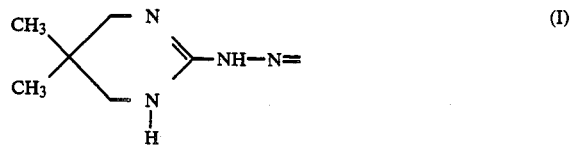

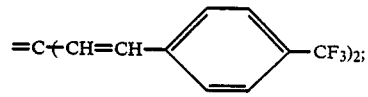

10% to 40% high fructose (55%) corn syrup; 0% to 10.0% isopropyl alcohol; 0% to 0.5% methyl p-hydroxbenzoate; and 25% to 60% of water; the composition having water to gellant ratios of 1.5/1 to 3.0/1 and a viscosity of 1.0 to $2.5 \times 10^6$ centipoise in a temperature range of 25° C. to 45° C.; a method of preparing the composition, and a method of its use.

6 Claims, No Drawings

GEL INSECTICIDAL COMPOSITIONS

This application is a continuation-in-part of application Ser. No. 06/764,363 filed Aug. 12, 1985, now abandoned.

SUMMARY OF THE INVENTION

The invention is an insecticidal gel composition especially useful for the control of cockroaches, a method of preparing the composition and a method of its use. More particularly, the invention relates to insecticidal gel compositions comprising tetrahydro-5,5-dimethyl-2(1H)pyrimidinone-{3-[4-(trifluoromethyl)phenyl]-1-{2-[4-(trifluoromethyl)phenyl]ethenyl}-2-propenylidene}hydrazone as a toxicant, a $C_{17}$–$C_{19}$ unsaturated fatty acid, or a $C_7$–$C_{17}$ saturated fatty acid or a mixture of the saturated and unsaturated fatty acids, propylene glycol, propyl p-hydroxybenzoate, high fructose (55%) corn syrup, methyl p-hydroxybenzoate a gelling agent and water; the compositions having a viscosity of 1.0 to $2.5 \times 10^6$ centipoise as measured with a Brookfield viscometer Model RVT with helipath stand T-D or T-E spindle, rotated at 0.5 rpm. The insecticide which is active as a stomach poison, can be graphically illustrated by formula (I) below.

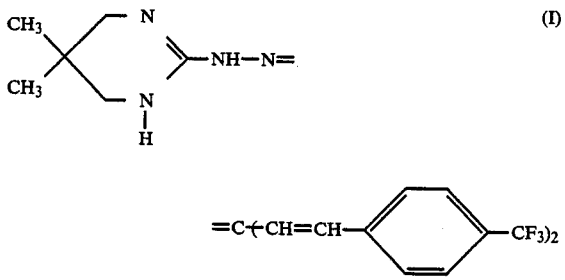

The formula I insecticide is disclosed and claimed in U.S. Pat. No. 4,163,102 and its method of use is claimed in U.S. Pat. No. 4,213,988, both of which are incorporated herein by reference. Insecticidal bait compositions of the abovenamed insecticide are disclosed in U.S. Pat. No. 4,320,130, which describes solid corn based baits which are suitable for application over large areas for the control of insects.

The novel insecticidal gel compositions of the invention are suitable for application within and around cockroach habitats. This type of application requires compositions which possess physical properties which make them suitable for application as a bead of material in corners and hard to reach places within structures which are inhabited by cockroaches. Applications of this type may be accomplished with tubes of material or caulking gun type applicators which apply the composition as a bead of material.

The gel compositions for the control of cockroaches comprise on a weight basis 14% to 22% of the gellant, 0% to 0.5% propyl p-hydroxybenzoate, 0% to 30% propylene glycol, 0.5% to 6% of a fatty acid such as a $C_{17}$–$C_{19}$ unsaturated fatty acid, a $C_7$–$C_{17}$ saturated fatty acid or a mixture of said fatty acids, 1% to 5% of formula (I) insecticide, 10% to 40% high fructose (55%) corn syrup, 0% to 10% isopropyl alcohol, 0% to 0.5% methyl p-hydroxybenzoate and 25% to 60% of water wherein the compositions have water to gellant ratios of 1.5/1 to 3.0/1.

Preferred unsaturated fatty acids useful in the preparation of compositions of the invention are oleic acid, linoleic acid, linolenic acid and abietic acid. Preferred saturated fatty acids are caprylic; capric, lauric, myristic, palmitic and stearic acids or mixtures thereof. The gellant selected is a non-ionic surfactant of structure α-hydro-Ω-hydroxy-poly(oxyethylene)poly(oxypropylene)poly(oxyethylene) block copolymer having an average molecular weight 12,500, mp 56° C., Brookfield viscosity of 3100 at 77° C., and surface tension of a 0.1% aqueous solution: 40.6 dynes/cm (measured with a du Nouy tensiometer).

The above described compositions have been found to be highly effective for the control of cockroaches when applied within structures. Additionally, it has been found that compositions of the invention having viscosities of 1.5 to $2.2 \times 10^6$ centipoise at room temperature (approximately 25° C.), which retain a viscosity equal to or greater than $1.0 \times 10^6$ centipoise at 45° C. are suitable for application as a bead which adheres upon application and does not run or drip after application. A preferred composition for the control of cockroaches is comprised of 50.4% water, 20.0% corn syrup, 0.2% methyl p-hydroxybenzoate, 2.0% oleic acid, 2.05% formula (I) insecticide, 0.15% propyl p-hydroxybenzoate, 7.2% propylene glycol, 18.0% of gellant on a weight basis. This preferred composition has a water to gellant ratio 2.8/1, and maintains an acceptable viscosity profile at 25° C. to 45° C. over time as shown in Table I below.

TABLE I

| Viscosity of preferred gel composition | | | |
|---|---|---|---|
| | Viscosity ($10^6$) centerpoise | | |
| | 25° C. | 37° C. | 45° C. |
| Initial | 2.0 | 1.8 | 1.6 |
| One month at 45° C. | 1.8 | 1.5 | 1.4 |
| Two months at 45° C. | 1.8 | 1.7 | 1.5 |

Stable gel compositions of the invention may be prepared by admixing a homogeneous mixture comprising the required quantities of water, corn syrup, methyl p-hydroxybenzoate and 70% to 90% on a weight basis of the above described gellant; with a homogeneous mixture containing the required quantities of tetrahydro-5,5-dimethyl-2(1H)pyrimidinone-{-[4-(trifluoromethyl)phenyl]-1-{2-[4-(trifluoromlethyl)phenyl]ethenyl}-2-propenylidene}hydrazone, a fatty acid such as a $C_{17}$–$C_{19}$ unsaturated fatty acid, a $C_7$–$C_{17}$ saturated fatty acid or a mixture of said fatty acids, propyl p-hydroxybenzoate isopropyl alcohol and propylene glycol until the final composition is homogeneous. The preparation may be conducted in a temperature range of 25° C. to 95° C. but temperatures below 80° C. may require the use of heavy duty mixing equipment such as a double planatary mixer, or Versa Mix equipped with a homogenizer or the like since the composition may gel in this temperature range. When the preparation is conducted above 80° C. the composition is a liquid. Upon completion of the preparation the composition which is either a liquid or gel, depending upon the temperature at which the preparation was conducted, may then be packaged. This procedure is suitable for the preparation of a variety of stable gel compositions as illustrated in Table II below.

TABLE II

| Component | % by weight |
| --- | --- |
| Water | 25.0–60.0 |
| Corn syrup | 10.0–40.0 |
| Methyl p-hydroxybenzoate | 0.0–0.5 |
| Oleic acid | 0.5–6.0 |
| Insecticidal toxicant | 1.0–3.0 |
| Propyl p-hydroxybenzoate | 0.0–0.5 |
| Propylene glycol | 0.0–30.0 |
| Isopropyl alcohol | 0.0–10.0 |
| Gellant | 14.0–22.0 |
| Water to gellant ratio | 1.5–3.0 |

The compositions prepared by the above procedure may then be applied within or about a structure which is infested with roaches. Use of these compositions has particular advantage, since such method of distribution poses little or no hazard to humans or animals that may frequent the infested area.

The invention is further illustrated by the examples set forth below. These examples are provided only by way of illustration and are not intended to be limiting.

EXAMPLE 1

Preparation of gel compositions

A premix is prepared by adding the solid gellant α-hydro-Ω-hydroxy-poly(oxyethylene)poly(oxypropylene)poly(oxyethylene) block copolymer, average molecular weight 12,500; mp 56° C.; Brookfield viscosity of 3100 at 77° C.; surface tension of a 0.1% aqueous solution: 40.6 dynes/cm (measured with a du Nouy tensiometer (160 g, 16%), to a homogeneous mixture of water (504 g, 50.4%), corn syrup (200 g, 20%), and methyl p-hydroxybenzoate (2 g, 0.2%), maintained at 85° C. to 90° C. in an evacuated and inerted nitrogen atmosphere. The resulting mixture is stirred at 85° C. to 90° C. until a homogeneous mixture is formed. A second homogeneous mixture is prepared by adding the formula (I) hydrazone (20.50 g, 2.05%) to a stirred solution of oleic acid (20 g, 2%), propyl p-hydroxybenzoate (15 g, 0.15%), gellant (20 g, 2%) in propylene glycol (72 g, 7.2%) at 50° C. to 60° C. under a nitrogen atmosphere. This mixture is then heated to 85° C. and added to the stirred homogeneous first premix maintained at 85° C. to 90° C. under a nitrogen atmosphere. After stirring until the composition is homogeneous, it is transferred to suitable containers, inerted with nitrogen and sealed.

Utilizing the above procedure and varying the amounts of propylene glycol and water, yields insecticidal gel bait compositions of varying water to gellant ratios, having acceptable gel ranges and viscosities as illustrated in Table III below.

TABLE III

Stable gel ranges for compositions containing 18% by weight gellant

| Composition | water/gellant | Gel range °C. | Viscosity ($10^6$) @ 25° C. |
| --- | --- | --- | --- |
| 1 | 2.3 | −20 to 102 | 2.1 |
| 2 | 2.4 | −16 to 100 | 2.0 |
| 3 | 2.5 | −12 to 98 | 2.0 |
| 4 | 2.6 | −10 to 94 | 1.9 |
| 5 | 2.7 | −6 to 90 | 1.75 |
| 6 | 2.8 | −4 to 86 | 1.6 |
| 7 | 2.9 | −1 to 83 | 1.5 |
| 8 | 3.0 | 1 to 80 | 1.4 |

EXAMPLE 2

Physical stability of gel compositions

The physical stability of composition 2 prepared in Example 1, having an initial viscosity of $2.0 \times 10^6$ centipoise at 25° C. is determined by storing aliquots at 25° C. and 45° C. and measuring the viscosities of the samples at 25° C., 37° C. and 45° C. at one month intervals (Brookfield viscometer Model RVT with helipath stand, TD spindle). The results of these experiments which are summarized in Table IV demonstrate the physical stability of the gel compositions with respect to maintaining desirable viscosities.

TABLE IV

Viscosity stability of gel composition

| | Viscosity ($10^6$) centipoise | | |
| --- | --- | --- | --- |
| | 25° C. | 37° C. | 45° C. |
| Initial | 2.0 | 1.8 | 1.6 |
| One month 45° C. | 1.8 | 1.5 | 1.4 |
| Two month 45° C. | 1.8 | 1.7 | 1.5 |

EXAMPLE 3

Efficacy of gel compositions

Samples of gel composition 2 prepared as described in Example 1 are applied as a 1/2 cm to 1 cm dab to the inside bottom surfaces of 30 mL clear plastic cups with holes cut in the sides to allow entry of the insects. One treated cup is placed in an inverted position in each one gallon cylindrical container along with a water source containing ten adult male German cockroaches (three replicates per treatment). Each container is covered with a piece of nylon netting held in place by a cardboard ring. Counts of live and dead cockroaches are made daily for four days and are reported as percent mortality compared to untreated controls. The results of these experiments which are summarized in Table V below demonstrate the efficacy of gel compositions of the above invention for control of cockroaches.

TABLE V

Efficacy of gel compositions against German cockroaches

| | Percent mortality (average of three replicates) Days exposure to bait | | | |
| --- | --- | --- | --- | --- |
| | 1 | 2 | 3 | 4 |
| Gel composition 2 | 0 | 67 | 100 | 100 |
| Untreated control | 0 | 0 | 0 | 0 |

EXAMPLE 4

Preparation and evaluation of formulations to determine the acceptability of the physical properties thereof Gel compositions are prepared in accordance with the procedure of Example 1 and the physical properties thereof determined by the procedure of Example 2.

| | Composition of Test Formulations | | |
| --- | --- | --- | --- |
| Ingredient | A | B | C |
| Water | 50.4 | 56 | 42.6 |
| Corn Syrup | 20.0 | — | 30.0 |
| Methyl p-hydroxybenzoate | 0.2 | — | 0.2 |
| Fatty Acid | 6.0 | 2.0 | 2.0 |

-continued

| Ingredient | Composition of Test Formulations | | |
|---|---|---|---|
| | A | B | C |
| | Mixture | Oleic Acid | Oleic Acid |
| Insecticide | 2.05 | 2.0 | 2.0 |
| Propylene glycol | 3.2 | 10.0 | 7.0 |
| Propyl p-hydroxybenzoate | 0.15 | — | 0.15 |
| Surfactant (Polawax) | — | 5 | 2 |
| Gellant | 18 | 25 | 14 |
| Viscosity @ R.T. | — | 3.2 | 0.3 |
| $10^6$ cps 37° C. | — | 2.8 | 0.15 |
| 45° C. | — | 1.6 | 0.07 |

In formulation A the fatty acid mixture has the following composition: capric acid 1%, lauric acid 55%, myristic acid 22%, palmitic acid 11%, stearic acid 3%, oleic acid 6% and lenoleic acid 2%.

The gellant in formulations A, B and C is α-hydro-Ω-hydroxy-poly(oxyethylene)poly(oxyprorylene)-poly(oxyethylene) block copolomer, average molecular weight 12,500, mp 56° C., Brookfield viscosity of 3100 at 77° C.

The insecticide in formulations A, B and C is tetrahydro-5,5-dimethyl-2(1H)-pyrimidinone-{3-[4-(trifluoromlethyl)phenyl]-1-{2-[4-(trifluoromlethyl)-phenyl]ethenyl}-2-propenylidene}hydrazone.

In formulations B and C, polawax surfactant is a nonionic ethoxylated fatty alcohol.

Examination of the gel formulations A, B and C, show that formulation A is an acceptable formulation having the proper consistency for ready application from a gel cartridge. This formulation forms an excellent gel bead that adheres to wood, polymer, concrete and metal surfaces and remains in place under normal conditions after application without running, slipping or smearing across to which it has been applied.

Formulation B has an unacceptable consistency. It is too thick to apply from a gel cartridge. The viscosity is $3.2 \times 10^6$ centipoise at room temperature.

Formulation C is also unsatisfactory. It is much too fluid to permit application as a gel bead from a gel cartridge. The viscosity of this formulation is $0.3 \times 10^6$ centipoise at room temperature.

What is claimed is:

1. An insecticidal gel composition comprising on a weight basis 14% to 22% of the gellant α-hydro-Ω-hydroxy-poly(oxyethylene)poly(oxypropylene)-poly(oxyethylene) block copolymer having an average molecular weight 12,500, mp 56° C., Brookfield viscosity of 3100 at 77° C., and surface tension of a 0.1% aqueous solution: 40.6 dynes/cm; 0.15% to 0.5% propyl p-hydroxybenzoate; 0% to 30% propylene glycol; 0.5% to 6% of a $C_{17}$–$C_{19}$ unsaturated fatty acid; a $C_7$–$C_{17}$ saturated fatty acid or a mixture of the fatty acids; 1% to 5% of formula (I) insecticide:

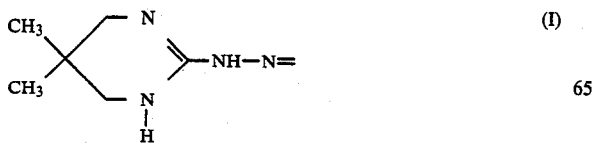

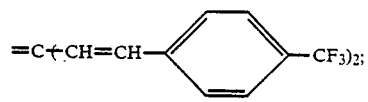

10% to 40% high fructose (55%) corn syrup; 0% to 10.0% isopropyl alcohol; 0.2% to 0.5% methyl p-hydroxybenzoate; and 25% to 60% of water; the composition having water to gellant ratios of 2.3/1 to 3.0/1 and a viscosity of $1.4 \times 10^6$ centipoise to $2.1 \times 10^6$ centipoise in a temperature range of 25° C. to 45° C.

2. A composition according to claim 1 comprising 50.4% water, 20.0% corn syrup, 0.2% methyl p-hydroxybenzoate, 2.0% oleic acid, 2.05% formula (I) insecticide, 0.15% propyl p-hydroxybenzoate, 7.2% propylene glycol, 18.0% of gellant on a weight basis.

3. A method for the preparation of an insecticidal gel composition comprising, admixing at 25° C. to 95° C. on a weight basis 14% to 22% of the gellant α-hydro-Ω-hydroxy-poly(oxyethylene)poly(oxypropylene)-poly(oxyethylene) block copolymer having an average molecular weight 12,500, mp 56° C., Brookfield viscosity of 3100 at 77° C., surface tension of a 0.1% aqueous solution: 40.6 dynes/cm; 0.15% to 0.5% propyl p-hydroxybenzoate; 0% to 30% propylene glycol; 0.5% to 6% of a $C_{17}$–$C_{19}$ unsaturated fatty acid; a $C_7$–$C_{17}$ saturated fatty acid or a mixture of the fatty acids; 1% to 5% of formula (I) insecticide

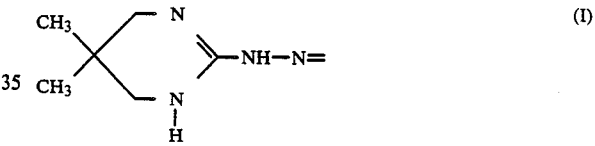

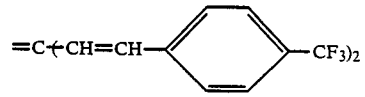

10% to 40% high fructose (55%) corn syrup; 0% to 10% isopropyl alcohol; 0.2% to 0.5% methyl p-hydroxybenzoate and 25% to 60% of water to obtain a composition having water to gellant ratios of 2.3/1 to 3.0/1 and a viscosity of $1.4 \times 10^6$ centipoise to $2.1 \times 10^6$ centipoise in a temperature range of 25° C. to 45° C.

4. A method according to claim 3 for preparing gel composition comprising, admixing on a weight basis 50.4% water, 20.0% corn syrup, 0.2% methyl p-hydroxybenzoate, 2.0% oleic acid, 2.05% formula (I) insecticide, 0.15% propyl p-hydroxybenzoate, 7.2% propylene glycol, and 18.0% of gellant.

5. A method for the control of cockroaches comprising
applying an insecticidally effective amount of an insecticidal gel composition on a weight basis if 14% to 22% of the gellant α-hydro-Ω-hydroxy-poly(oxyethylene)poly(oxypropylene)poly(oxyethylene) block copolymer having an average molecular weight 12,500, mp 56° C., Brookfield viscosity of 3100 at 77° C., surface tension of a 0.1% aqueous solution: 40.6 dynes/cm; 0.15% to 0.5% propyl p-hydroxybenzoate; 0% to 30% propylne glycol; 0.5% to 6% of a $C_{17}$–$C_{19}$ unsaturated fatty acid; a $C_7$–$C_{17}$ saturated fatty acid or a mixture of the fatty acids; 1% to 5% of tetrahydro-5,5-dimethyl-2(1H)pyrimidinone-{3-[4-(trifluoromethyl)phenyl]-1-{2-[4(trifluoromlethyl)phenyl]ethenyl}-2-propenylidene}hydrazone insecticide; 10% to 40% high fructose (55%) corn syrup; 0% to 10.0% isopropyl alcohol; 0.2% to 0.5% methyl p-hydroxybenzoate; and 25% to 60% of water; the composition having water to gellant ratios of 2.3/1 to 3.0/1 and a viscosity of $1.4 \times 10^6$ centipoise to $2.1 \times 10^6$ centipoise in a temperature range of 25° C. to 45° C.

in an area where cockroaches will have access to the composition.

6. A method according to claim 5 comprising applying a composition of 50.4% water, 20.0% corn syrup, 0.2% methyl p-hydroxybenzoate, 2.0% oleic acid, 2.05% insecticide, 0.15% propyl p-hydroxybenzoate, 7.2% propylene glycol and 18.0% of gellant on a weight basis.

* * * * *